(12) United States Patent
Park

(10) Patent No.: US 11,266,420 B2
(45) Date of Patent: Mar. 8, 2022

(54) SPARSE CONTACT FEMORAL JIG MECHANISM

(71) Applicant: Unik Orthopedics, Inc., Fremont, CA (US)

(72) Inventor: Ilwhan Park, Walnut Creek, CA (US)

(73) Assignee: Unik Orthopedics, Inc., Fremont, CA (US)

( * ) Notice: Subject to any disclaimer, the term of this patent is extended or adjusted under 35 U.S.C. 154(b) by 85 days.

(21) Appl. No.: 14/820,451

(22) Filed: Aug. 6, 2015

(65) Prior Publication Data

US 2018/0296226 A1    Oct. 18, 2018

Related U.S. Application Data

(60) Provisional application No. 62/034,085, filed on Aug. 6, 2014, provisional application No. 62/034,078, filed on Aug. 6, 2014.

(51) Int. Cl.
*A61B 17/15* (2006.01)
*A61B 17/17* (2006.01)

(52) U.S. Cl.
CPC ........ *A61B 17/155* (2013.01); *A61B 17/1764* (2013.01)

(58) Field of Classification Search
CPC ...... A61B 17/15; A61B 17/151; A61B 17/155
See application file for complete search history.

(56) References Cited

U.S. PATENT DOCUMENTS

| 5,593,411 | A  | * | 1/1997 | Stalcup | A61B 17/1764 606/87 |
| 7,104,997 | B2 | * | 9/2006 | Lionberger | A61B 17/155 606/88 |
| 7,201,755 | B2 | * | 4/2007 | Faoro | A61B 17/155 606/88 |
| 8,211,113 | B2 | * | 7/2012 | Brown | A61B 17/1615 606/96 |
| 8,419,740 | B2 | * | 4/2013 | Aram | A61B 17/155 606/88 |
| 9,033,991 | B2 | * | 5/2015 | Salehi | A61B 17/155 606/88 |
| 9,408,619 | B2 | * | 8/2016 | Salehi | A61B 17/155 |
| 9,855,061 | B2 | * | 1/2018 | Amos | A61B 17/155 |

* cited by examiner

*Primary Examiner* — Anu Ramana
(74) *Attorney, Agent, or Firm* — Blue Capital Law Firm, P.C.

(57) ABSTRACT

A femur cutting jig mechanism (FCJM) is provided having a number N1 of spaced apart FCJM contact points that correspond to a number N1 of spaced apart femur contact points on at least one of a medial condyle, a lateral condyle, and a trochlear groove on the patient's knee. The FCJM contact points are positioned in contact with the knee contact points, and a cut bar mechanism is positioned in contact with the FCJM to provide a location and an angular orientation of a cut bar plane that is to be used to resection and remove a selected portion of the patient's, knee. The FCJM is removed from the patient's knee, and a selected portion of the patent's knee is resectioned and removed. The number N1 is at most 12 in some embodiments.

10 Claims, 15 Drawing Sheets

SPARSE CONTACT FEMORAL JIG MECHANISM

RELATED APPLICATIONS

This application claims priority under 35 U.S.C. § 119 from U.S. provisional application No. 62/034,078 entitled "SPARSE CONTACT FEMORAL JIG MECHANISM," filed on Aug. 6, 2014, the entire contents of which are fully incorporated by reference herein for all purposes. This application also claims priority under 35 U.S.C. 119 from U.S. provisional application No. 62/034,085 titled "METHOD FOR CREATING A CUSTOMIZED ARTHROPLASTY RESECTION GUIDE UTILIZING TWO-DIMENSIONAL IMAGING," filed on Aug. 6, 2014, the entire contents of which are fully incorporated by reference herein for all purposes.

TECHNICAL FIELD

This invention relates to orthopedic procedures for knee replacement.

BACKGROUND

Traumatic knee injuries, such as ligament tears and meniscus tears, degenerative joint diseases, such as arthritis, and overall wear and tear can necessitate repair or replacement of the knee joint in an "arthroplasty" procedure. A conventional arthroplasty procedure involves remodeling, realigning and in some instances the total or partial replacement of the damaged knee joint with prosthetic implants. For example, in a total knee replacement procedure, a portion of the femur and tibia, where they come together at the knee joint, are removed and replaced with a femoral shell and a mating tibial plate, respectively, that together function like a healthy knee joint.

To assist in arthroplasty procedures, and particularly partial or total knee replacements, a jig may be used to position any one of a number of possible instruments used to drill, cut, and shape or otherwise operate on the damaged knee area. In the particular case of a total knee replacement, a jig may be positioned on the femur to mount a cutting guide that in turn supports a bone saw or other tool to cut (resect) a portion of the distal region of the femur. Similarly, a jig may be positioned on the tibia to mount a cutting guide that in turn supports a bone saw or other tool to resect a portion of the proximal region of the tibia. After the femur and tibia are prepared, the surgeon mounts the femoral shell and tibial plate.

Images of orthopedic joints that are candidates for partial or total replacement are often formed as MRI images, referred to here as "slices," with each such image being a projection on a two dimensional image forming substrate. Each such MRI image is actually a three dimensional "voxel," representing a thickness of approximately 2 mm of partial images of cortical bone, cancellous bone cartilage and open space, with each such material having its own range of grey scales in the MRI image. For a full three dimensional representation of an anatomical surface AS of interest, it is often necessary to provide tens to hundreds of MRI slices in two or more of three views (coronal or front view, axial or top view, and sagittal or side view) for a given anatomical component.

Many of the knee replacement procedures presently use what is characterized as "full segmentation" in order to represent a relevant portion of a femur or a tibia surface in three dimensions. This approach requires use of a dense, three dimensional grid of points to accurately represent a surface, especially a surface having cusps or sharp corners with very small associated radii of curvature. This approach has several disadvantages, including the following: (1) this approach is time consuming, often requiring 4-20 hours of intense numerical work to generate and check the accuracy of the grid point coordinates for a single surface; (2) because of the time required to implement this approach for a single surface, use of this approach in mass manufacturing of custom or semi-custom instruments is limited; (3) this approach may introduce geometrical errors, including closing errors; (4) because of the close spacing of grid points, polynomials of high mathematical degree are be used, which can introduce undesirable "ripples" in the mathematical surface produced by a full segmentation process; and (5) formation and analysis of a large number of MRI slices is required.

It is with these observations in mind, among others, that aspects of the present disclosure were conceived and developed.

SUMMARY

One aspect of the present disclosure involves a cutting jig for positioning a femur cutting tool on a femur including a first condyle and a second condyle with a trochlear groove defined therebetween, the femur further including an intercondylar fossa. The cutting jig may include a substrate or other apparatus or structure that includes a plurality of jig contact points. For example, the substrate may include:

a first jig contact point oriented to contact the first condyle proximate the trochlear groove when the jig is positioned on the femur for a procedure a second jig contact point oriented to contact the second condyle proximate the trochlear groove when the jig is positioned on the femur for a procedure, the second jig contact point coronolly spaced apart from the first jig contact point;

a third jig contact point proximate the first jig contact point, the third jig contact point oriented to contact the first condyle when the jig is positioned on the femur for a procedure;

a fourth jig contact point proximate the second jig contact point when the jig is positioned on the femur for a procedure, the fourth jig contact point oriented to contact the second condyle;

a fifth jig contact point oriented to contact the first condyle when the jig is positioned on the femur for a procedure, the fifth jig contact point posteriorly positioned relative to the first jig contact point;

a sixth jig contact point oriented to contact the second condyle when the jig is positioned on the femur for a procedure, the fifth jig contact point posteriorly positioned relative to the second jig contact point;

a seventh jig contact point oriented to contact the first condyle proximate the intercondylar fossa when the jig is positioned on the femur for a procedure;

an eighth jig contact point oriented to contact the second condyle proximate the intercondylar fossa when the jig is positioned on the femur for a procedure;

a ninth jig contact point oriented to contact the first condyle when the jig is positioned on the femur for a procedure, the ninth jig contact point posteriorly positioned relative to the seventh jig contact point; and a tenth jig contact point oriented to contact the second condyle when the jig is positioned on the femur for a procedure, the tenth jig contact point posteriorly positioned relative to the eighth jig contact point.

The jig may also include a cut guide, which may be integrated with the substrate or be provided by a cutting guide attached thereto that provides the cut guide, which may be in the form of a slot or other mechanism by which a surgeon may resect the femur along an established cut plane transverse the femoral axis and typically associated with a partial or total knee replacement procedure.

DETAILED DESCRIPTION

It would be desirable to eliminate the full segmentation process and the associated three dimensional anatomical modeling of a femur surface, and to replace this approach with data obtained from relatively few MRI "slices," as few as, for example, six two-dimensional slices, that permits flexibility in choice of contact points between the femur surface and the instrument (jig) that facilitates resectioning and removal of a portion of the knee component. It would be even more desirable to replace the full segmentation procedure, with its thousands of grid points, with a simpler, quicker procedure that works with as few as about twelve contact points between an anatomical surface, such as the posterior femur, and a resectioning mechanism, such as a jig that properly positions a cutting guide.

Aspects of the present disclosure involve a "sparse contact" approach that provides a cutting jig mechanism, which provides a cut plane for a femur 6 component of a knee 8. A lower (distal) portion of the femur component, illustrated in FIGS. 1A and 1B for a right knee, includes a lateral condyle (LC) 10 and an adjacent medial condyle (MC) 12, which together define a trochlear groove (TG) 14 that is positioned between the lateral and medial condyles, and extends from the anterior of the respective condyles posteriorly to the intercondylar fossa 16 between the posterior of each respective condyle. Each condyle is of generally convex shape with the intersection between the condyles forming the trochlear groove being concave. The remainder of the femur is positioned above the lateral and medial condyles.

Figure 1A:
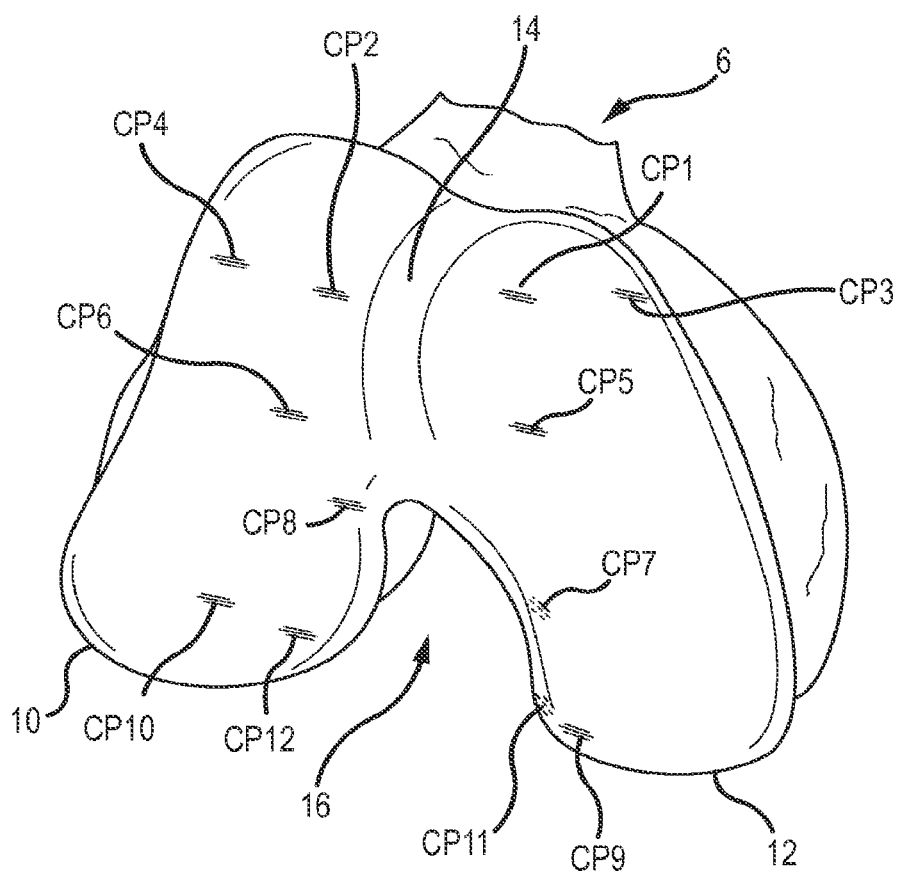
FIG. 1A is a representative isometric view of a lower portion of a femur (right knee), indicating contact points for a fibia cutting jig mechanism (FCJM) in one embodiment.
Figure 1B:
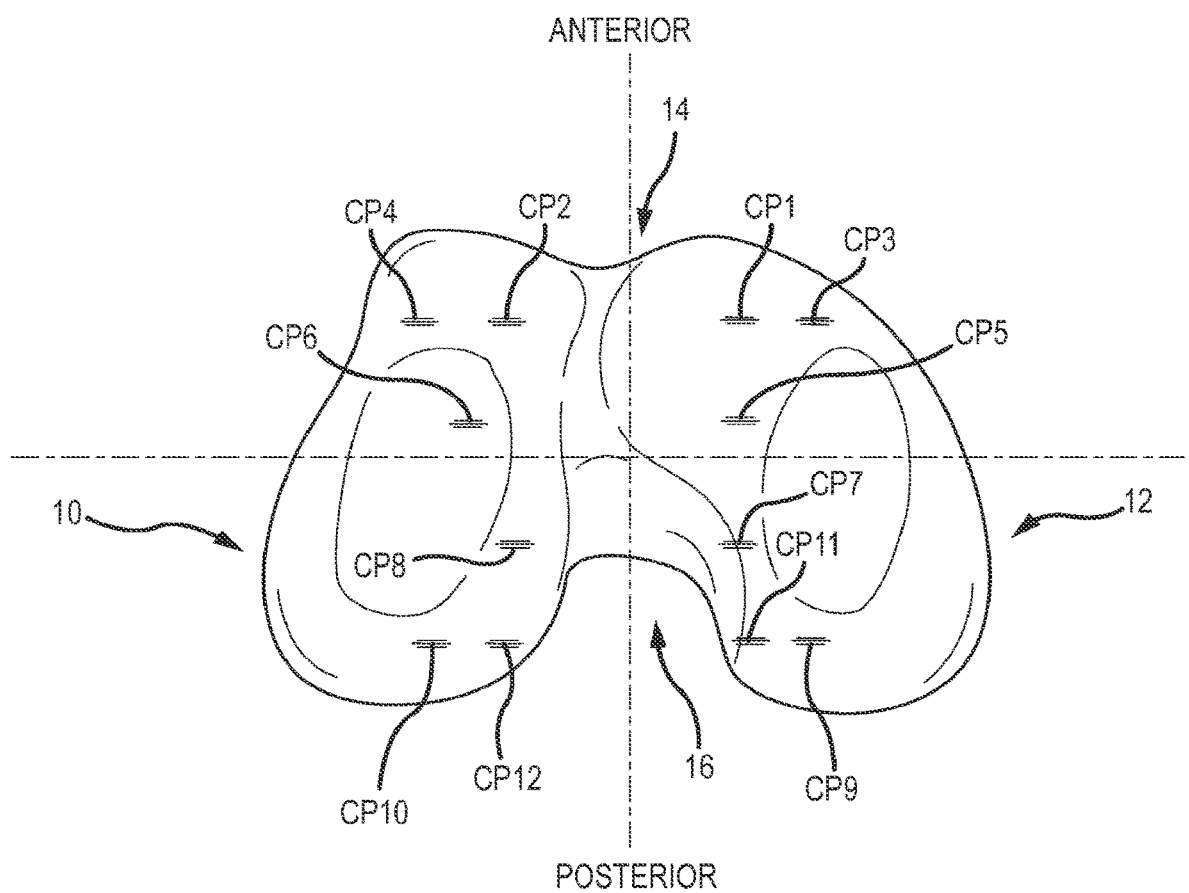
FIG. 1B is a representative top view of the lower portion of the femur as shown in FIG. 1A.
Figure 2A:
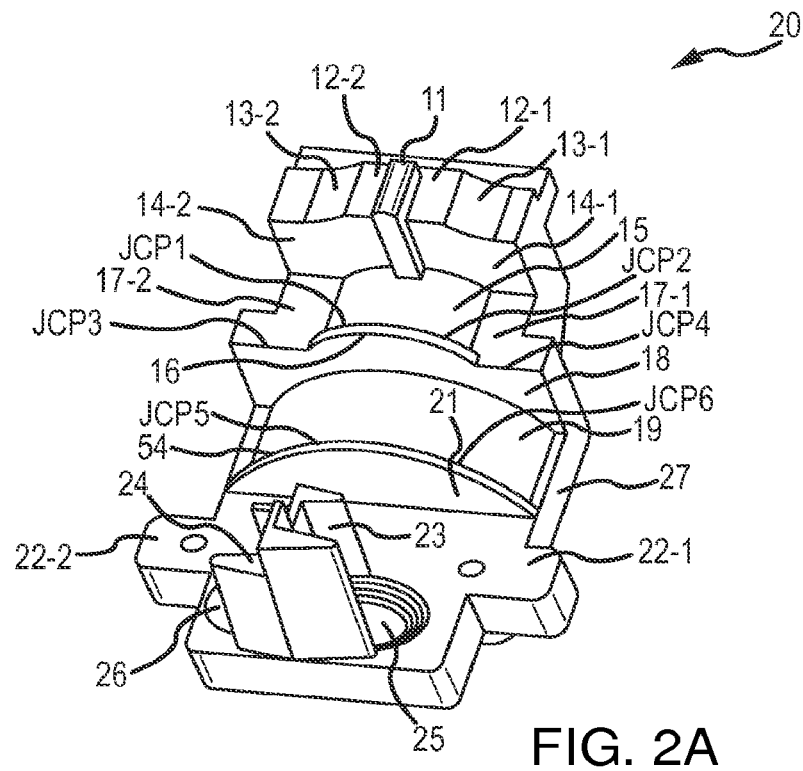
FIGS. 2A and 2B are isometric views of a femur cutting jig mechanism, indicating contact points that correspond to the contact points indicated in FIG. 1A, in one embodiment.
Figure 2B:
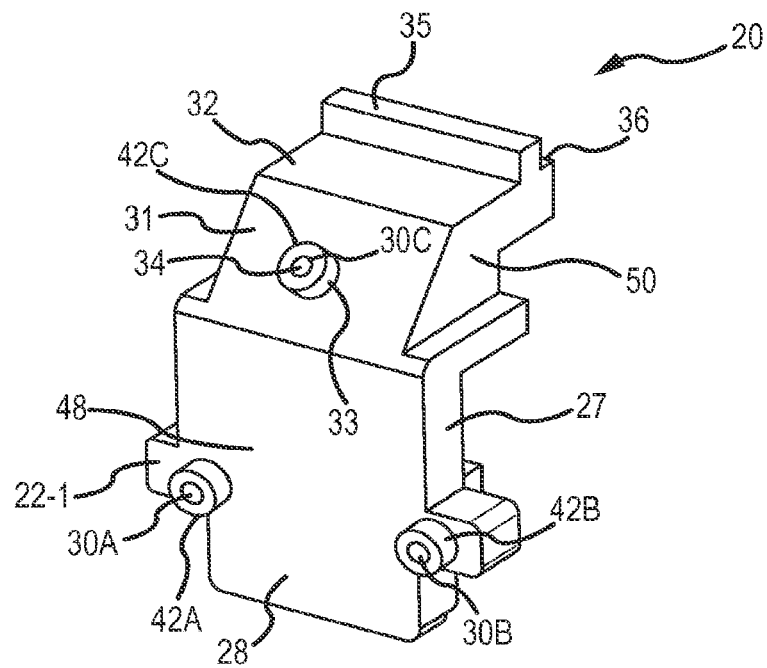

A femur cutting jig mechanism (FCJM or "jig") 20, illustrated in isometric views in FIGS. 2A and 2B and in FIGS. 3A-3E with the jig positioned on or relative to the femur 6, has a first number N1 of jig contact points (JCPs) that make contact with a small number of corresponding femoral contact points (CPs in FIGS. 1A and 1B) on the trochlear groove surface 14 of the femur, and/or on the respective condyles to either side and adjacent to the trochlear groove, and make contact with a second number N2 of contact points on the lateral condyle 10 and on the medial condyle 12, where the sum, N1+N2, may be about 12, and can be made smaller in some approaches. The number, N1+N2, of contact points and their placement on the femur surfaces is chosen so that, where each jig contact point makes contact with a corresponding contact point on the femur surface, the jig is stably positioned on the femur surface and resists any longitudinal, transverse, and/or rotational forces of modest magnitude that would otherwise move the jig. In this way, a surgeon may position the jig onto the femoral surface and when the various contact points are positioned and mildly pressed on the femur, the jig resists various forces that would cause it to move so long as some mild force is maintained to hold the jig in place. The jig may then be pinned to the femur and used to mount a cutting guide on the femur. When the jig contact points are properly positioned, the jig seats on the femur in accordance with a cut plane. When the femur is resected along the cut plane, a prosthetic may be placed on the femur in accordance with a determined prosthetic knee alignment.

Figure 3A:
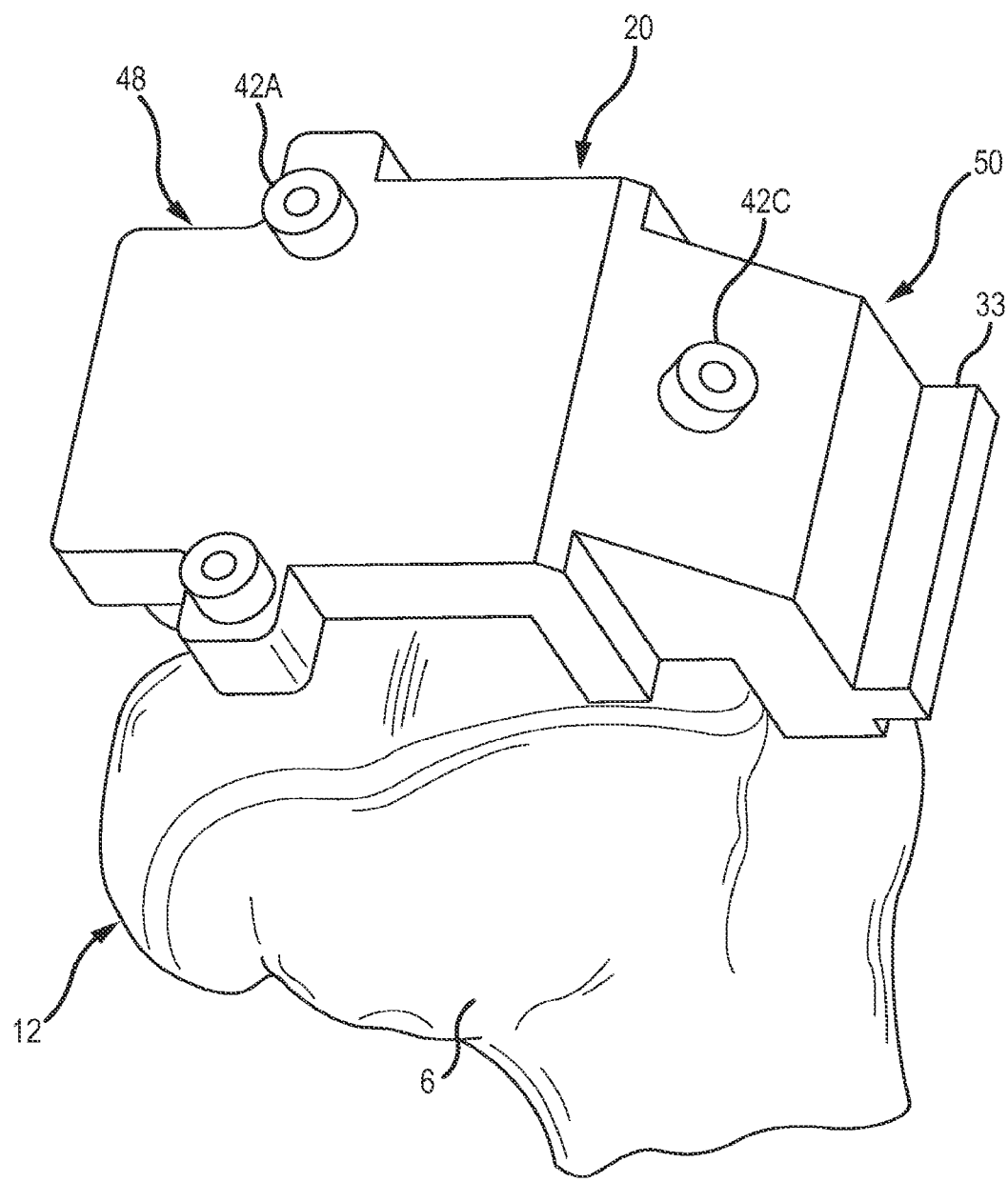
FIGS. 3A, 3B, and 3C illustrate various isometric views of one example of a FCJM on a distal region of a femur.
Figure 3B:
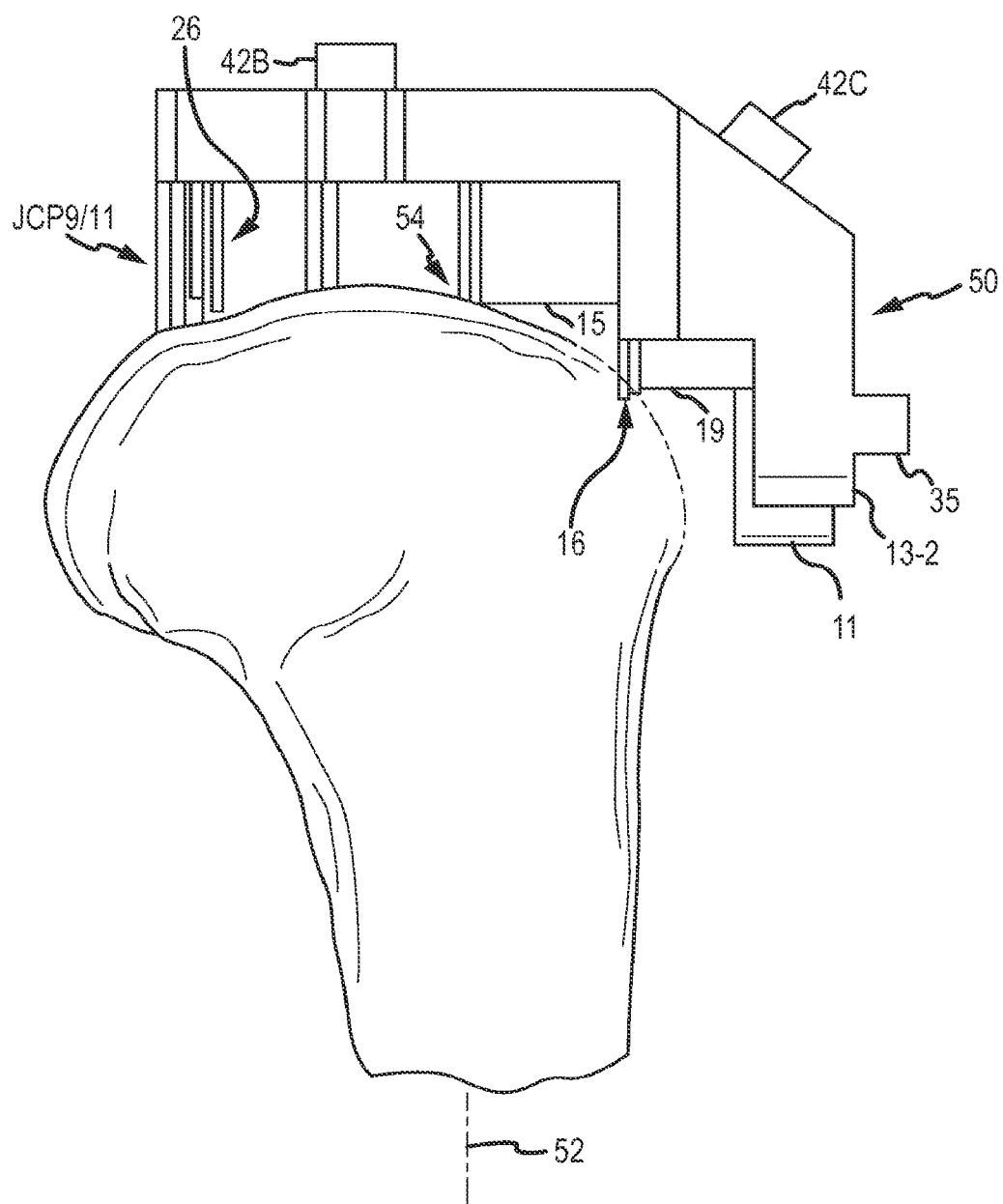
Figure 3C:
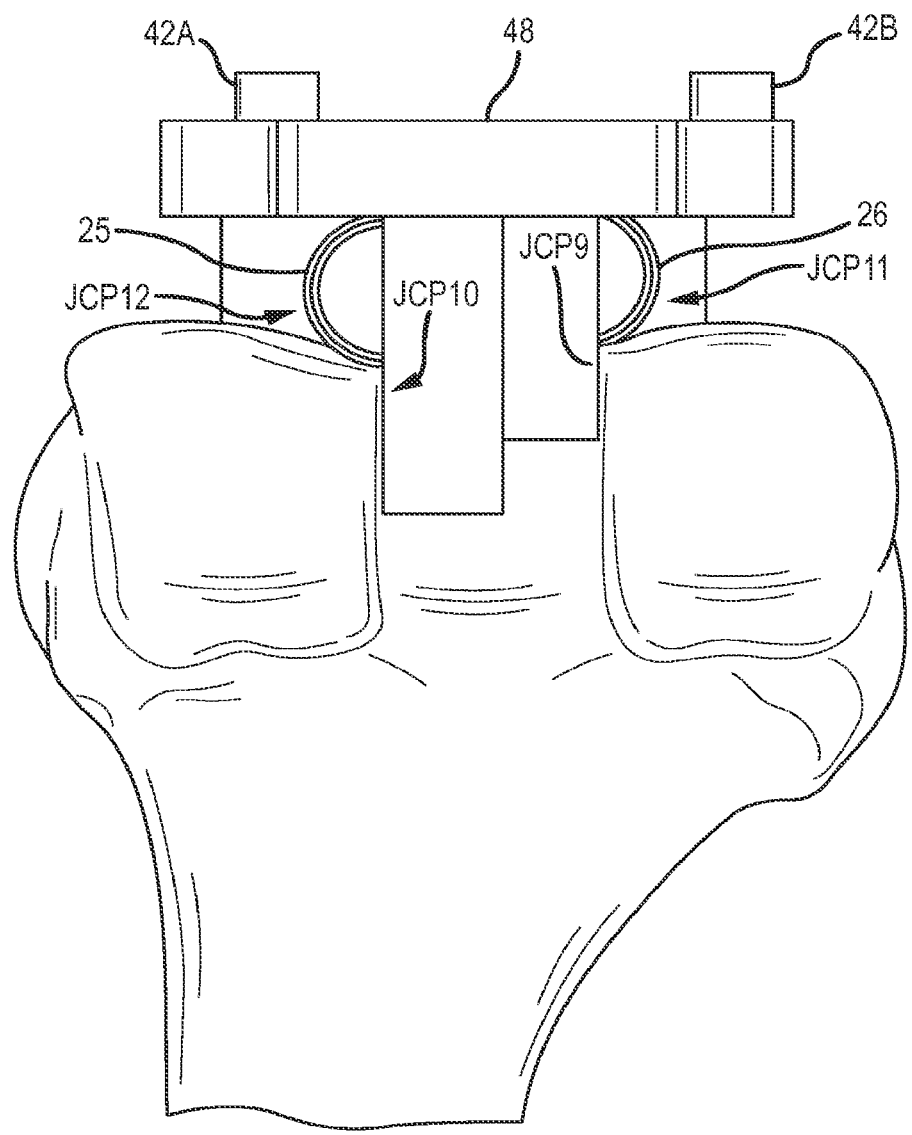
Figure 3D:
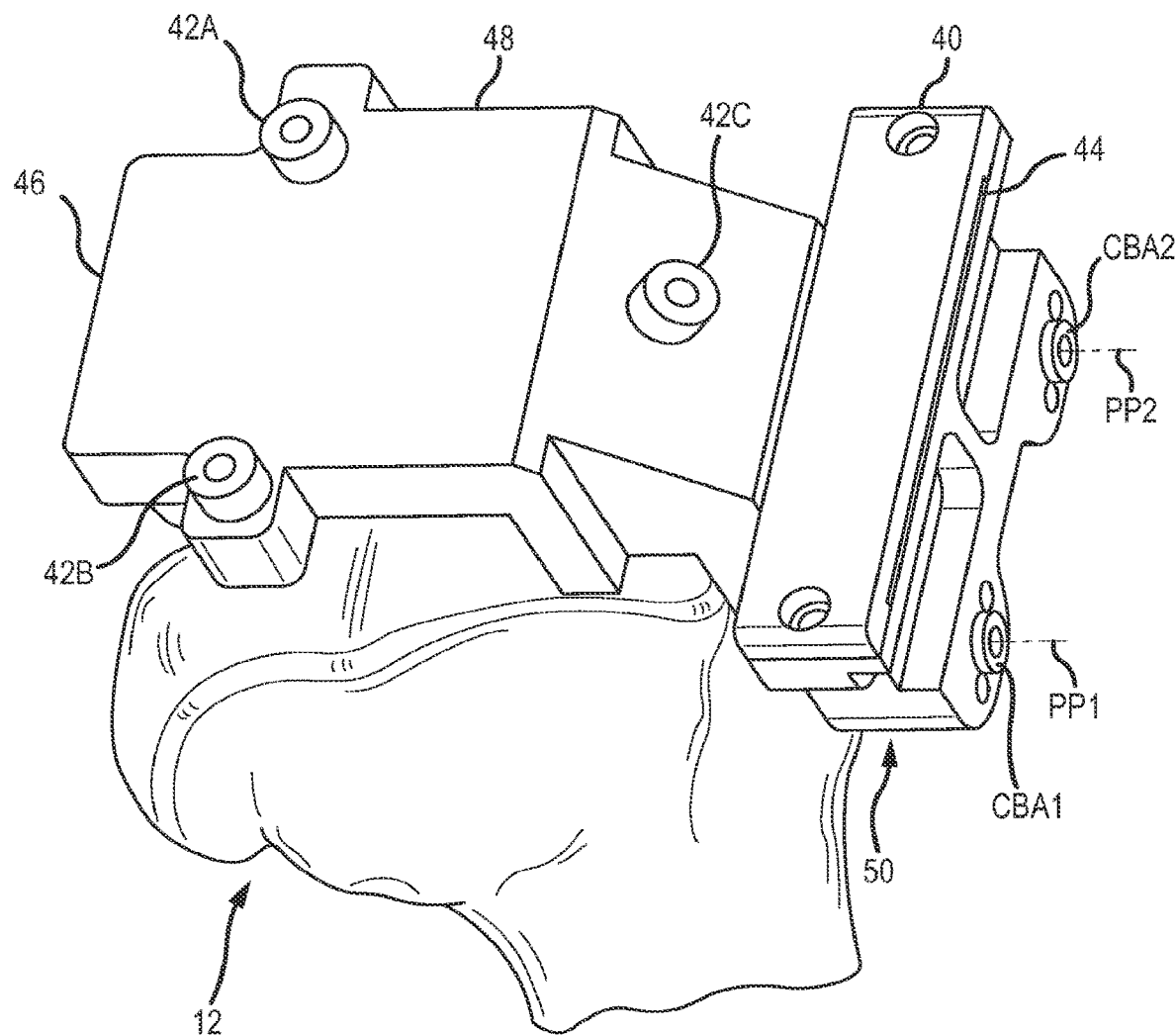
FIG. 3D illustrates an axial isometric view of the FCJM on the distal region of the femur, with a cut plane bar coupled with a mounting flange of the FCJM.
Figure 3E:
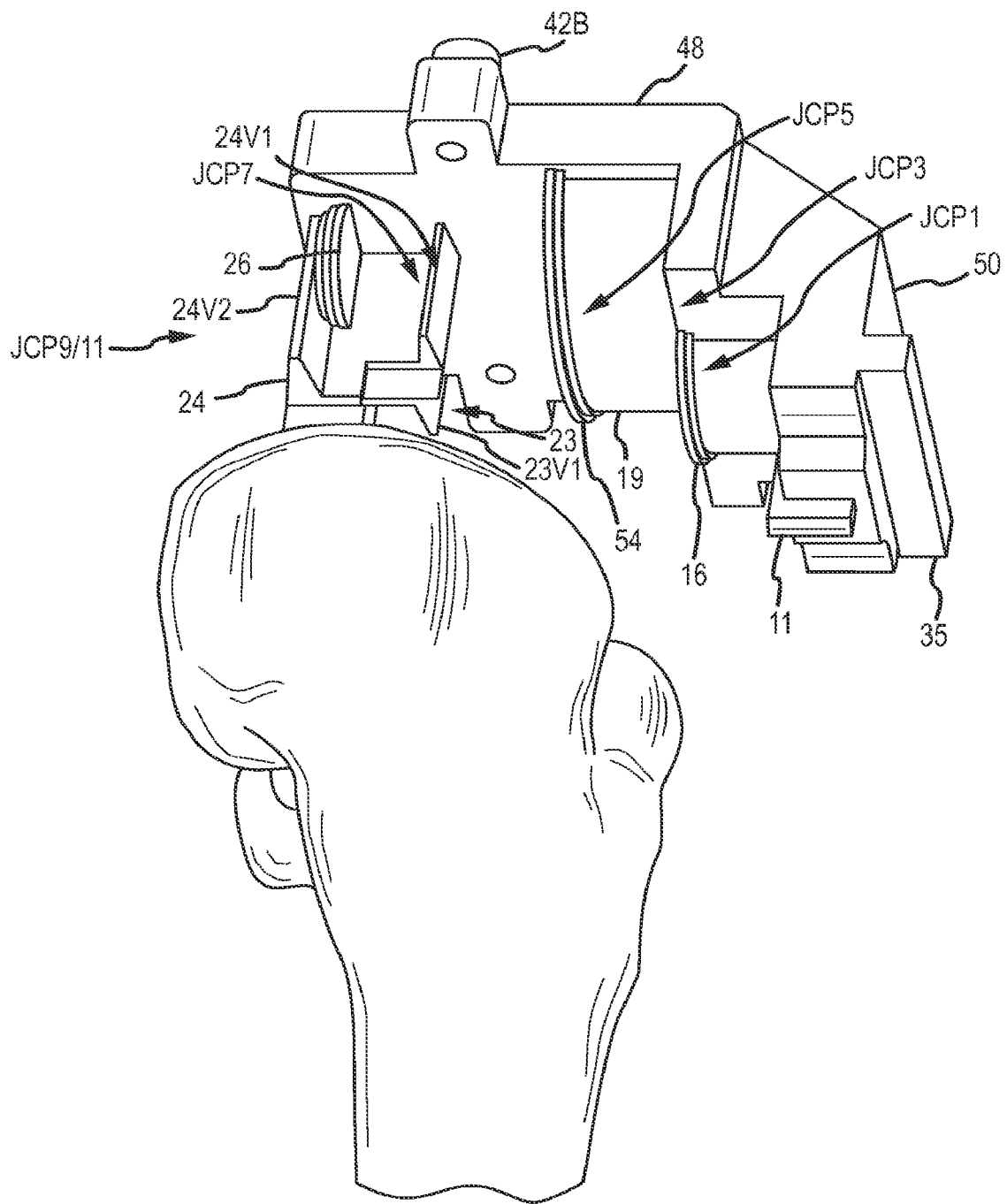
FIG. 3E illustrates the jig positioned above the femur prior to placement thereon.

Referring to FIGS. 3A-3E, more particularly, the jig 20 and a corresponding cut plane guide 40 (FIG. 3D) are positioned in contact with the condyles 10, 12 of the femur, and with the trochlear groove 14. FIGS. 3A-3E illustrate the jig slightly above and not fully in contact with the femur. The jig, once positioned correctly, is pinned to the femur by inserting three pins (not shown) through three corresponding bosses 42A, 42B, 42C projecting from the jig and defining apertures 30A, 30B, 30C through which the pins are inserted. It may be necessary to predrill the femur prior to placement of the pins. The cut plane bar is mounted to a mounting flange 35, and is pinned to the femur through two cut bar positioning apertures, CBA1 and CBA2, shown in FIG. 3D and defined in the cut plane guide 40. To secure the CPG, a surgeon drills into a portion of cortical bone, using CBA1 and CBA2 as guides. Two positioning pins, PP1 and PP2, are inserted into the apertures, CBA1 and CBA2, and into the drilled out portion of the cortical bone. Referring to FIG. 3B, the surgeon may then remove the jig by removing the three jig pins, and rotating the mounting flange 35 away from the cut plane guide and then withdrawing the jig away from the femur, leaving the guide in place. The jig, when mounted on the femur, pre-positions the mounting flange and the cut plane guide. The cut plane guide defines a slot (or channel) 44 positioned so that a bone saw may be guided to resection and remove a lower portion of the patient's femur, for replacement of the knee. After resectioning has occurred, the guide is removed and optionally can be reused in replacement of another patient's knee.

The "sparse contact" approach described herein relies on a small number (e.g., six or fewer) of spaced apart two-dimensional MRI images or "slices" of the femur anatomical surface, with each slice containing or illuminating one, two, or possibly more contact points between the femur anatomical surface and the jig 20 that helps define a cut plane position for resectioning and removing a portion of the femur. Using this approach, more than one jig contact point may be defined for a slice so that some jig contact points may be co-planar relative to the MRI slice and or relative to each other. The approaches discussed herein may have several advantages, including but not limited to: (1) the number of MRI slices actually formed and used is quite small (e.g., about 6) and represents about 5-10 percent of the total volume of the portion of the anatomy component of interest; (2) the number of contact points and associated coordinates needed for position stability of the jig is also small (e.g., about 12 or less, as compared with hundreds to thousands for a full segmentation approach); (3) the "design time" required to determine relevant component dimensions and coordinates of the contact points on the anatomical surface is estimated to be no more than 20 minutes and should decrease further as one accumulates experience in the dimensioning process; (4) it is anticipated that this "sparse contact" approach will permit semi-custom design and fabrication of the replacement components and associated tools; and/or (5) provides some flexibility for the orthopedic surgeon to exercise creativity and compensation in choices and modifications of some of the dimensions and angular orientations.

A femoral cutting jig 20 conforming with various aspects of the present disclosure includes a substrate 46 from which various jig contact points (JCPm) project, are otherwise supported or defined. In one possible implementation, the jig is a unified structure formed from a block of base material using a computer numerical control (CNC) machine. However, it is possible for the jig to be an assembly of various components that form the final cutting jig structure. Alternatively, the jig may be created through molding, machining, milling, forming, 3D printing, assembling, or other processes. The term "substrate" as used herein is meant to refer to a base structure upon which the various jig contact points and jig contact point supporting structures are provided or otherwise supported, and by which the relative positioning of the various jig contact points are maintained. As mentioned, the jig may be a unified structure and hence the substrate and jig contact points are formed from the same material and thus the relative positioning of the jig contact points is naturally maintained. Other processes, such as milling a base material or forming a jig in a mold, would provide a similar unified structure. It is not necessary, however, that the jig be unified structure in which case the substrate may be a frame or other structure or assembly on which various jig contact point defining structures are attached or otherwise associated.

The jig contact points are arranged and spaced such that a surgeon may press the jig onto the distal surface of the femur at the knee and the jig will be properly positioned when the jig contact points are seated on respective femoral contact points (CPm). Notably, there are a discrete number of jig contact points (e.g., 9-14) as opposed to full surfaces or far more numerous numbers of contact locations. The jig also includes a cutting guide support structure onto which may be mounted the cutting guide 40. When the jig is seated on the femur, the jig may be pinned to the femur to properly position the cutting guide so that a resection of the femur may be performed pursuant to a total knee replacement.

Referring now to FIGS. 2A and 2B, and 3A-3E, the jig includes a first substrate portion 48 and a second substrate portion 50 generally perpendicular the first substrate portion. The relative position and orientation between the first substrate portion and the second substrate portion need not be perpendicular, however. As can be seen in FIG. 3B, the first substrate portion 48 is generally transverse to a femoral axis 52 of the femur 6 (substantially in the axial plane when mounted) and the second substrate portion 50 is generally perpendicular to the first substrate portion (substantially in the coronal plane when mounted). It should be noted that the jig positions the cut plane bar, and hence the jig position on the femur will vary based on the anatomy of the patient, the type of procedure, the type of prosthetic, and any number of other factors. Hence, the anatomical relationships described are illustrative and not limiting.

Beginning at the trochlear groove end of the jig 20, a vertical projection 11 (FIG. 2A) is located at the center of an anterior end of the second substrate portion 50. The vertical projection provides a visual queue or reference for a surgeon. When the jig is properly positioned on the femur, the central vertical projection aligns visually with the anterior proximal end region of the trochlear groove 14. In the specific jig shown, the vertical projection is positioned on and between a first and a second horizontal surface, 12-1 and 12-2, which are in turn positioned between first and second curved, descending concave surfaces 13-1 and 13-2, which may be formed by tooling elements, such as from CNC machine router bits. The descending surfaces are formed from the removal of material, and the material may be removed to allow a surgeon to see past the vertical projection to where the points along the curvilinear surface 16 contact the respective condyles 10, 12 to either side of the trochlear groove as discussed in further detail below. The features 11, 12-1, 12-2, 13-1, and 13-2 are bounded on a first side by first and second vertical surfaces, 14-1 and 14-2, of the second substrate portion. The various features discussed and shown herein are but one way to create a jig defining the various jig contact points of interest. In the example shown, the CNC machine tool bits and other cutting mechanisms influence the jig shapes. The various surfaces and jig features, on which the jig contact points are defined, are thus defined in part by requirements of the CNC machine. If the jig were formed in another way, such as through 3D printing or molding, the jig contact point features and overall jig shape may be different than illustrated although the position and relative location of the jig contact points, depending on the patient, would be substantially the same regardless of the jig manufacturing technique employed.

The implementation of the jig illustrated herein includes two curvilinear (e.g., partial circle or section) trochlear groove surfaces, with each surface defining two jig contact points (JCP1, JCP2 and JCP5, JCP6) configured to engage respective first and second femoral contact points (CP1 and CP2) and respective fifth and sixth contact points (CP5 and CP6) to either side of the trochlear groove 14 adjacent the respective condyles. More specifically, a first curved surface 15 defining the first jig contact point (JCP1) and the second jig contact point (JCP2). The first and second jig contact points contact respective first and second femoral contact points (CP1 and CP2). In the specific implementation illustrated, the surface 15 defines a curvilinear lip 16, which is bounded between the first and second vertical surfaces 14-1, 14-2, a third and a fourth horizontal surface, 17-1 and 17-2, and vertical surface 18. A third jig contact point JCP3 and a fourth jig contact point JCP4 are defined along a boundary between the respective horizontal surfaces 17-1/17-2 and a third vertical surface 18. The jig contact points JCP3 and JCP4 may be in the same plane as JCP1 and JCP4 (substantially parallel to the femoral axis), and contact respective femoral contact points CP3 and CP4, on the respective lateral and medial condyles adjacent the trochlear groove with points CP1 and CP2 above points CP3 and CP4, respectively on the lateral and medial condyles. Stated differently, the contact points CP3 and CP4 may be on the portions of the condyles facing each other at the trochlear groove 14, and may be on the walls of the groove itself, and the respective points CP3 and CP4 medially and laterally, respectively, CP1 and CP2.

As discussed throughout, the jig structure illustrated is a convenience of manufacturing, with the jig originally formed from a block of material and machined away to form the resulting structures. It is possible to also define a curvilinear surface 16 as a discrete planar element extending from the first substrate portion, and defining the curvilinear (arcuate) surface with contact points JCP1 and JCP2. Jig contact points JCP3 and JCP4 may be defined using a planar rectangular element, a radial planar element, or other structures. In the implementation shown, the surface 15 is machined to a smaller size relative to the 16 so that the jig contact points defined along surface 16 may contact the appropriate femur surface without unintentional contact by surface 15. Since the groove 14 descends away from the jig when positioned, the arced surface shape 15 is believed to not interfere with the groove while at the same time not requiring extensive machine time. The surface 16 may be machined to a greater extent than illustrated but such machining would require greater time and is not believed to be required for most patients. Finally, should there be contact between surface 15 and the knee, the shape is believed to allow the surgeon to press the jig into place and ensure proper contact between the jig contact points and the femur contact points.

The third vertical surface 18 bounds the first curved surface 15 and bounds the third and fourth horizontal surfaces, 17-1 and 17-2. The third vertical surface 18 is bounded on one side by a second curved surface 19 defining fifth and sixth jig contact points JCP5 and JCP6, which contact respective femoral contact points CP5 and CP6. In the specific implementation shown, the contact points are defined along a second curved surface lip 54, bounded on one side by a fourth vertical surface 21. The contact points CP5 and CP6 are on the respective lateral and medial condyles 10, 12, and posterior relative to the contact points CP1 and CP6. Stated differently, the contact points CP5 and CP6 are on the respective lateral and medial condyles or the portion of the groove 14 adjacent thereto, at the posterior region of the trochlear groove 14 adjacent the intercondylar fossa 16. As with other surfaces, projections and the likely structure illustrated is a convenience of manufacturing, with the jig originally formed from a block of material and machined away to form the resulting jig contact points JCP5 and JCP6. It is possible to also define a curvilinear surface 54 as a discrete planar element extending from the first substrate portion 48, and defining the curvilinear (arcuate) surface with contact points JCP5 and JCP6. The first curvilinear surface 16 is concentric with the second curvilinear surface 20.

As illustrated, there are six jig contact points defined to contact the respective lateral and medial condyles to either side of the trochlear groove. In the embodiment shown, there are four contact points defined along two curvilinear arcuate surfaces 16 and 54. The arcuate surfaces are defined to fit down within the space above groove with portion of the arcs touching the groove or respective condyles. The respective condyles are generally rounded and come to a peak region where the contact points CP3 and CP4 are defined and where the planar/linear surfaces 17-1, 17-2 may define the jig contact points JP3 and JP4. In this way, the jig may be placed down on the femur and the jig contact points may touch and seat against the respective femoral contact points.

A first and a second horizontal plateau projection, 22-1 and 22-2, each with an aperture, 30A and 30B defined therein, extend transversely adjacent to the fourth vertical surface 21 and are part of the first substrate, in one possible implementation. As shown in FIG. 2B, the apertures extend through the respective bosses 42A and 42B extending from the first substrate, and on a side of the jig away from where the jig contacts the femur. A diagonally oriented surface 31 extends from the first substrate 48 to a fifth vertical surface 32. The diagonal surface 31 has the boss 42C and an aperture 30C therein. The fifth vertical surface is contiguous to a rectangle bar 35 for cut bar orientation, which lies between the fifth vertical surface and a sixth vertical surface 36, and to which the cut plane bar 40 is mounted.

With respect now to contact points adjacent the intercondylar fossa 16, six additional jig contact points may be defined that cooperate with the first six contact points discussed above, to secure the jig to the femur for a procedure. More particularly, first and second curvilinear quadrilaterals, 23 and 24, extend from the first substrate and are contiguous to each other. The quadrilaterals may be generally parallel the second substrate portion 50. The vertical surfaces are part of the second substrate portion. Additionally, adjacent and outward from the quadrilaterals, two curvilinear surfaces 25 and 26 project from the first substrate. Collectively, the quadrilaterals and curvilinear surfaces define jig contact points JCP7-JCP12 that contact respective femoral contact points CP7-CP12 lying on the lateral and medial condyles adjacent the intercondylar fossa 16. More specifically, as shown in FIGS. 1A and 1B, the contact points CP7, CP9 and CP11 lie on an inner surface of the medial condyle (facing the fossa and lateral condyle) successively posterior relative to the groove 14 and adjacent the intercondylar fossa 16. Contact points CP8, CP10, and CP12 lie on an inner surface of the lateral condyle (facing the fossa and medial condyle) also successively posterior relative to the groove 14 and adjacent the intercondylar fossa. CP7 may be coplanar to CP8, CP9 may be coplanar to CP10, and CP11 may be coplanar to CP12, in planes substantially parallel the femoral axis 52. The planes are substantially parallel but will deviate from parallel depending on numerous factors including the femur axis relative to the knee and cut plane, the type of procedure, the degree of degeneration the knee and the jig form to deal with the same, and other anatomical and/or requirements of the procedure.

Figure 4A:
FIGS. 4A-4I illustrate two dimensional, closed and open, linear and curvilinear formats that can be used to construct tangent lines and other linear and curvilinear approximation elements used in obtaining relevant dimensions in different embodiments, illustrated in an example in FIG. 4J.

FIGS. 4A through 4I illustrate some two dimensional, linear and curvilinear formats that can be used in embodiments to construct tangent lines, other approximation elements (FIG. 4J), and geometrical structures that provide one more jig contact points along a surface thereof. Stated differently, various geometric shapes may be used to define a jig contact point and FIG. 4 provides various examples of such shapes. Referring first to FIG. 4J, a portion of an MRI slice is illustrated. The MRI slice shows a line 56 denoting a boundary of the femur where a femur contact point 58 is located and where a corresponding jig contact point 60 is defined, which will contact the fibia at the femur contact point. The femur portion illustrated may be cortical bone, cancellous bone or cartilage at a boundary to open space or otherwise. Because each such material may have its own range of grey scales in the MRI image, the line is merely representative of a contact area, which may not be in fact a discrete line. The femur contact area of the MRI may be a slice through all or a portion of either or both condyles, the trochlear groove, the femur shaft, or other regions of the distal area of the femur relevant to a total knee replacement procedure or other femoral procedure that may take advantage of the jig described herein.

In the view illustrated in FIG. 4J, a portion of a coronal plane MRI slice of the distal femur is illustrated. More specifically, the line represents a coronal plane MRI slice of the lateral condyle encompassing a femoral contact point 58 (e.g., CP1). In order to define a jig contact point 60 (e.g., JCP1), various lines and geometrical shapes may be deployed. In the case of FIG. 4A, a rectangle is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal rectangle (length and width) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a rectangular contact point defining structure or other structures, the structure may be made to intersect or touch the femoral contact area of interest at and with coinciding tangent lines.

Figure 4B:

In the case of FIG. 4B, a line segment is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal line (length) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a linear contact point defining structure or other structures, the structure may be made to intersect or touch the femoral contact area of interest at and with coinciding tangent lines.

Figure 4C:

In the case of FIG. 4C, a circle is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal circle (center and radius) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a circular contact point defining structure or other structures, the structure may be made to intersect or touch the femoral contact area of interest at and with coinciding tangent lines.

Figure 4D:

In the case of FIG. 4D, an ellipse is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal ellipse (center and radius) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of an elliptical contact point defining structure or other structures, the structure may be made to intersect or touch the femoral contact area of interest at and with coinciding tangent lines.

Figure 4E:
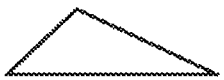

In the case of FIG. 4E, a triangle is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal triangle (base and height) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a triangular contact point defining structure or other structures, the structure may be made to intersect or touch the femoral contact area of interest at and with coinciding tangent lines.

Figure 4F:

In the case of FIG. 4F, a trapezoid is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal trapezoid (base and height) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a trapezoidal contact point defining structure or other structures, the structure may be made to intersect or touch the femoral contact area of interest at and with coinciding tangent lines.

Figure 4G:

In the case of FIG. 4G, a parallelogram is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal parallelogram (base and height) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a parallelogram contact point defining structure or other structures, the structure may be made to intersect or touch the femoral contact area of interest at and with coinciding tangent lines.

Figure 4H:

In the case of FIG. 4H, a quadratic curve is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal quadratic curve (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a quadratic curve contact point defining structure or other structures, the structure may be made to intersect or touch the femoral contact area of interest at and with coinciding tangent lines.

Figure 4I:
Figure 4J:
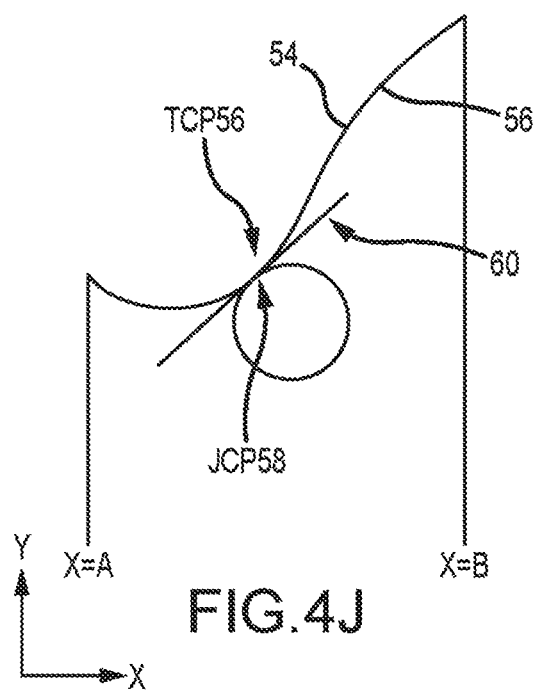
Figure 5A:
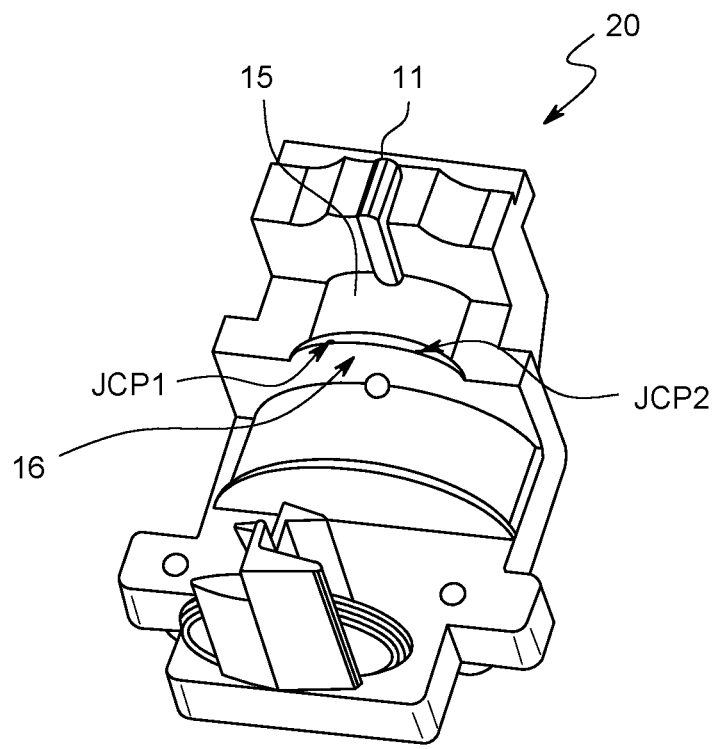
FIGS. 5A-5B are isometric and schematic views indicating suitable locations of FCJM contact points, according to an embodiment.
Figure 5B:
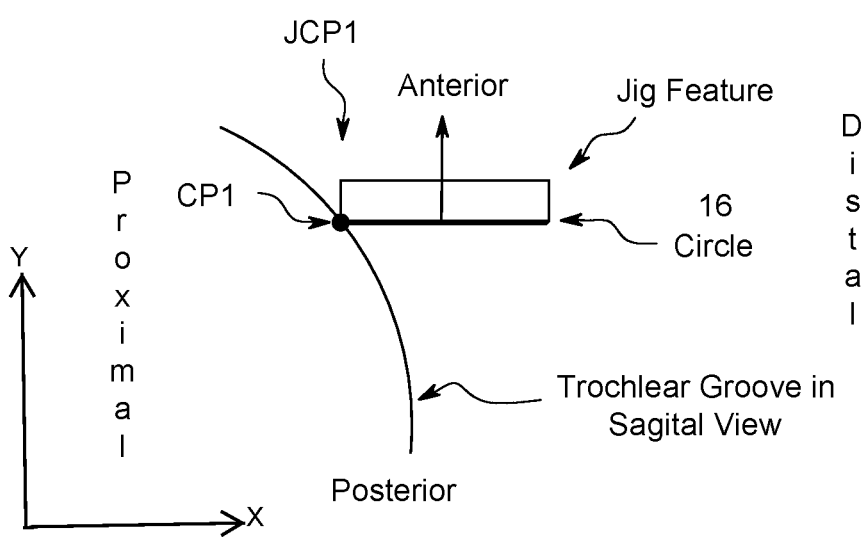

In the case of FIG. 4I, a cubic curve is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal cubic curve (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a cubic curve contact point defining structure or other structures, the structure may be made to intersect or touch the femoral contact area of interest at and with coinciding tangent lines.

FIG. 4J, illustrates the use of a circle to define the jig contact point at the corresponding femoral contact point. Depending on the implementation, it may be preferable that no corner point, such as a jig contact point, be sharp or otherwise have a high degree of sharpness such as is often associated with a true "point"; rather, a contact point may have an associated point radius segment that is at least about 0.3 mm in actual size or larger up to and including a line, in one possible implementation. The incorporation of this constraint will help ensure that, for example, a jig contact point will have adequate frictional contact such that the contact point will not slip or otherwise move relative to a region on the femur but at the same time the contact point will not penetrate or pierce any soft tissue on the portion of the femur being contacted which would possibly distort the fit of the jig to the femur. It is less of a concern about damaging the femur as the portion of the femur being contacted is likely to be removed (resected) and replaced with a prosthetic implant. Notably, if a linear segment surface, such as a segment of a square, rectangle, triangle or trapezoid, is used as the contact point defining structure, and a corner of such structure is not the contact point, the area along the linear segment surface at which contact is made, is considered to be a contact point. Moreover, in such an implementation, the linear segment surface may have a rounded or otherwise non-knife edge cross section, particularly at the area where the surface is intended to contact the femur.

FIGS. 5-10 will now be discussed with additional reference to the various jig contact points. FIG. 5A is an isometric view of an embodiment of the jig 20, showing suitable positions for jig contact points, JCP1 and JCP2. FIG. 5B is a representative sagittal plane view of the lateral condyle area containing CP1 and illustrating the jig feature 16 (e.g., a portion of a circle) defining the jig contact point (JCP1) contacting the lateral condyle/trochlear groove at CP1. Referring to FIGS. 5A, 1A and 1B, with the femur size illustrated, the contact points CP1 and CP2 are spaced apart approximately 1.5 cm and lie on the semi-circle 16 with a radius determined by a radius r(15) (millimeters). Accordingly, the first curved surface 16 (FIG. 2A) defines the radius r(15), which will cause JCP1 and JCP2 to contact the femur at CP1 and CP2 with about 1.5 cm of spacing therebetween. Of course, with a larger or smaller sized femur or differently spaced and/or shaped condyles and trochlear groove, the contact points may be more or less separated, and typically with spacing between 11 mm and 19 mm, although variations outside of this range are possible. As indicated in a sagittal view of a portion of the trochlear groove, with the jig in contact with the respective condyles of the lower femur (FIG. 5B), each of the contact points, JCP1 and JCP2, can move anteriorly (indicated by the vertical upward arrow), but cannot move posteriorly (downward), because of the presence of a solid object—a portion of the trochlear groove and the respective condyles where jig contact points (JCP1 and JCP2) contact the respective femoral contact points (CP1 and CP2) when the jig is pressed on the femur.

Figure 6A:
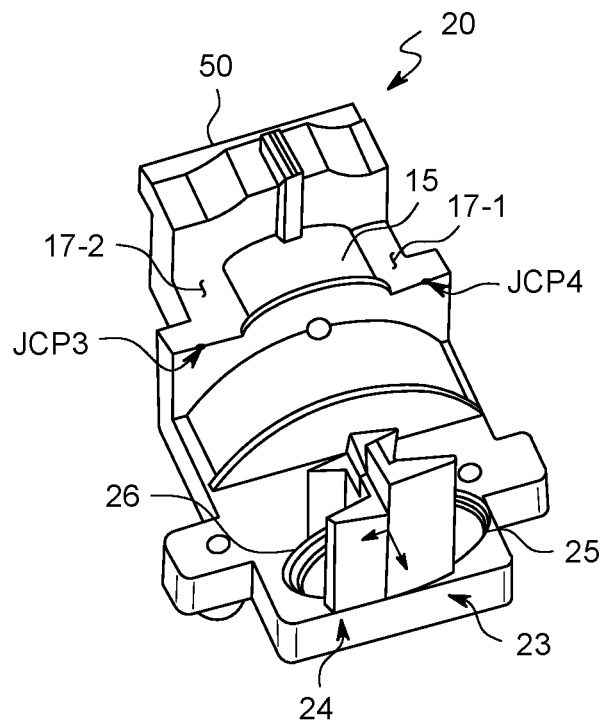
FIGS. 6A-6B are isometric and schematic views indicating suitable locations of FCJM contact points, according to an embodiment.
Figure 6B:
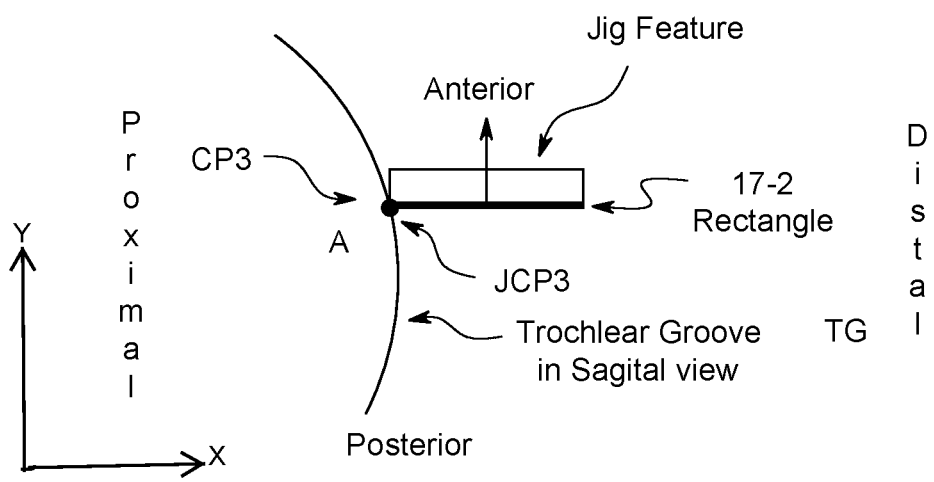

FIG. 6A is an isometric view of the jig 20, showing one or two suitable positions for jig contact points, JCP3 and JCP4. FIG. 6B is a representative sagittal plane view of the lateral condyle containing CP3 and illustrating a jig feature (a portion of rectangle) defining the jig contact point JCP3 contacting the lateral condyle at CP3. The femoral contact points CP3 and CP4 are spaced apart approximately 2 cm, but will typically fall within a range of 15 mm to 25 mm, depending on patient anatomy with variations outside this range possible. In the implementation illustrated, CP3 and CP4 are in the same sagittal plane as CP1 and CP2. Similarly, JCP3 and JCP4 are in the same sagittal plane as JCP1 and JCP2. However, such a coplanar arrangement is not necessary. In the specific implementation illustrated in FIG. 6A, JCP3 and CJP4 lie on the third and fourth horizontal surfaces, 17-1 and 17-2 (shown in FIG. 2A), and particularly along edge regions co planar with the lip 16 defining JCP1 and JCP2. While illustrated as surfaces, the contact points may also be defined on a rectangular planar projection extending from the substrate. Alternatively, the contact points may be defined on other surfaces or projections. For example, it would be possible to form the contact points on a circular surface, similar to the surface supporting contact points JCP1 and JCP2. However, with a CNC machine formed jig, the surface is an efficient and effective way to define the third and fourth jig contact points. Similar to the relation between JCP1 and JCP2, and as indicated in a sagittal view of a portion of the trochlear groove TG with the jig in contact with the lower femur (FIG. 6B), each of the jig contact points, JCP3 and JCP4, can move anteriorly (indicated by the vertical upward arrow), but cannot move posteriorly (downward), because of the presence of a solid object—a portion of the trochlear groove and the respective condyles where jig contact points (JCP3 and JCP4) contact the respective femoral contact points (CP3 and CP4) when the jig is pressed on the femur.

Figure 7A:
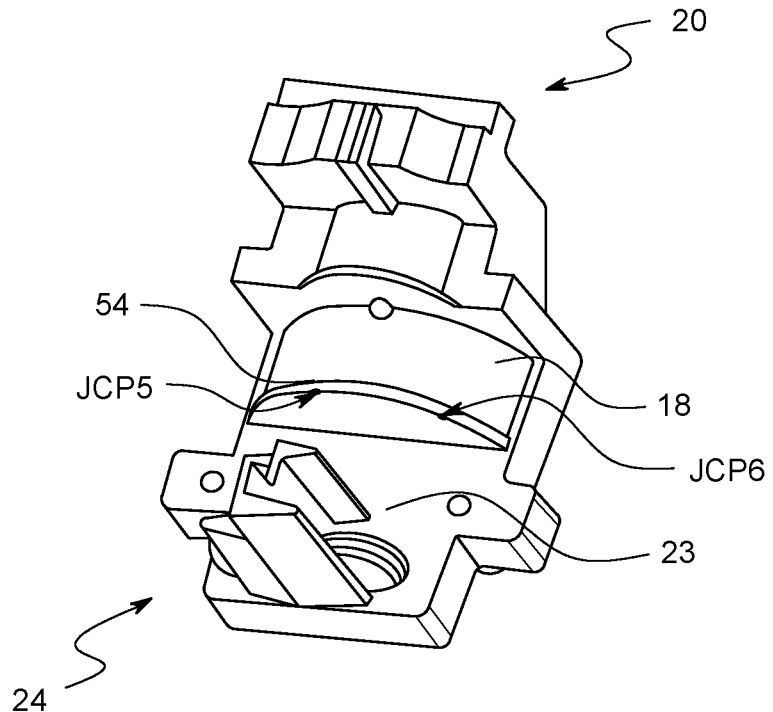
FIGS. 7A-7B are isometric and schematic views indicating suitable locations of FCJM contact points, according to an embodiment.
Figure 7B:
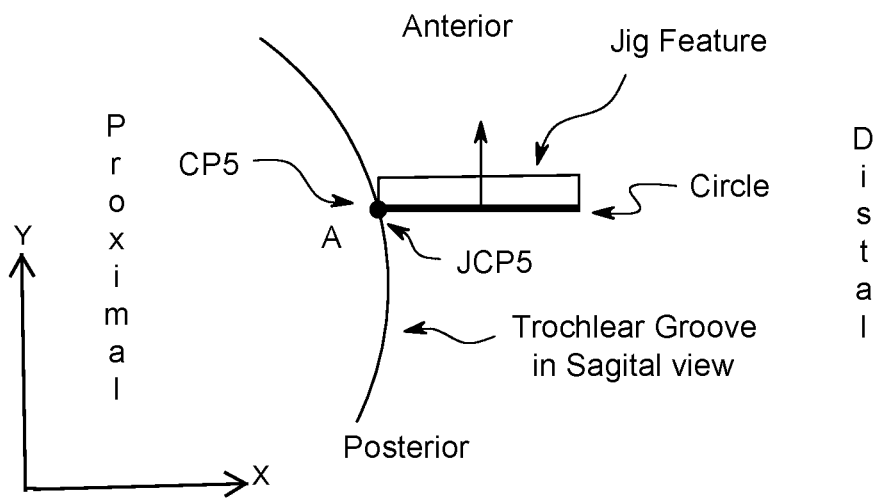

FIGS. 7A and 7B are isometric and schematic views of an embodiment of the jig, showing one or two suitable positions for jig contact points, JCP5 and JCP6, which contact the femur at respective contact points CP5 and CP6. The contact points CP5 and CP6 are spaced apart approximately 2.5 cm, but may typically fall within a range of 21 mm to 29 mm, although deviations outside this range are possible. Contact points CP5 and CP6 are positioned posteriorly relative to contact points CP1-CP4. The jig contact points lie on the semi-circular surface 54, which may have a radius determined by a radius r(18) (millimeters). Since the separation between CP5 and CP6, across the trochlear groove, is larger than the separation between CP1 and CP2 across the trochlear groove, the radius of the curvilinear (e.g. partial circular) surface 54 is larger than the radius of the curved surface 16. It is also possible to define a different structure to provide contact points CP5 and CP6. For example, a trapezoid defining a face at both JCP5 and JCP6 could be used, with the faces being defined along a tangent to the femur surface at CP5 and CP6. In another example, a discrete triangle defining respective surfaces at JCP5 and JCP6 might be deployed, again with a face of the triangle defined along a tangent to the femur surface at CP5 and CP6. As indicated in a sagittal view of a portion of the trochlear groove TG (FIG. 7B), with the jig in contact with the femur lower portion, each of the contact points, CP5 and CP6, can move anteriorly (indicated by vertical upward arrow), but cannot move posteriorly (downward), because of the presence of a solid object.

Figure 8:
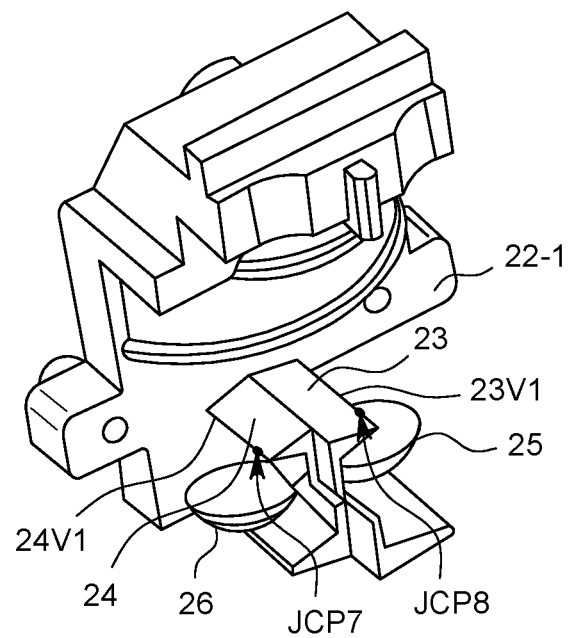
FIG. 8 is an isometric view indicating suitable locations of FCJM contact points (7-8), according to an embodiment.

FIGS. 8-10B illustrate jig contact points defined on the extending quadrilaterals of the vertical projection 11, and partial circular projections 25, 26, from the first substrate portion 48 at a region distal the second substrate portion 50. FIG. 8 is an isometric view of the jig 20, showing one or two suitable positions for jig contact points, JCP7 and JCP8, that contact the femur at contact points CP7 and CP8 on the respective inner portions of the lateral and medial condyles adjacent to the intercondylar fossa 16. The jig contact points JCP7 and JCP8 lie on first vertices, 23V1 and 24V1, of the first and second curvilinear quadrilaterals, 23 and 24. The jig contact points are spaced apart approximately 2 cm, but may typically be in a range of 16 mm to 24 mm depending on patient anatomy. In the example illustrated, the quadrilaterals have a substantially triangular cross section, with intersection side walls coming together to define the respective vertices 23V1 and 24V1. The vertices are rounded and otherwise do not define a knife edge, in the implementation illustrated. The contact points lie in substantially the same sagittal plane but are offset slightly in the axial plane, with the contact points being on the inner portions of the respective condyles proximate to the intercondylar fossa. In contrast to jig contact points JCP1-JCP6, jig contact points JCP7 and JCP8 can move posteriorly but are restricted from move anteriorly by the shape of the condyles and fossa. Here, the contact points are constrained by the respective inner (adjacent) portions of the lateral and medial condyles, as those features become closer together anteriorly.

Figure 9:
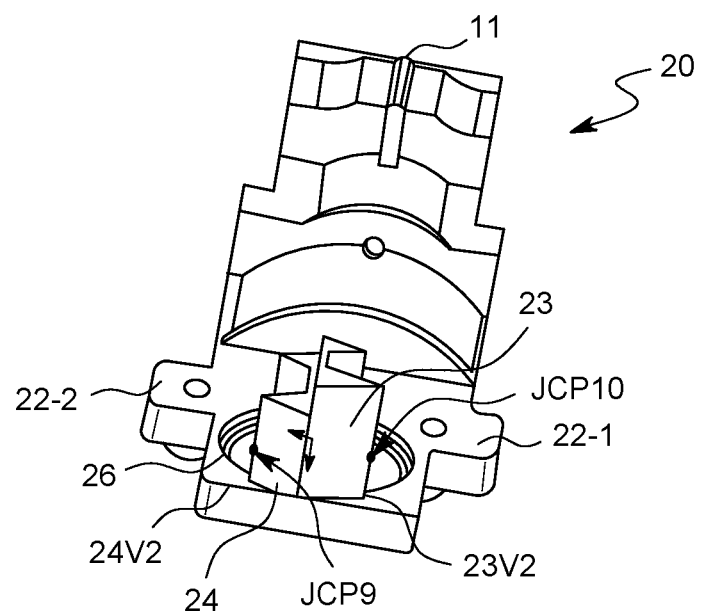
FIG. 9 is an isometric view indicating suitable locations of FCJM contact points (9-10), according to an embodiment.

FIG. 9 is an isometric view of the jig 20, showing one or two suitable positions for jig contact points, JCP9 and JCP10, that contact the femur at contact points CP9 and CP10 on the respective inner portions of the lateral and medial condyles posteriorly from contact points CP7 and CP8, and near the posterior end regions of the respective condyles. The contact points CP9 and CP10 lie on second vertices, 23V2 and 24V2, of the first and second curvilinear quadrilaterals, 23 and 24, and are spaced approximately 3 cm apart, but may typically be in a range of 26 mm to 34 mm depending on patient anatomy, although variations outside that range are possible. In the example illustrated, the quadrilaterals have a substantially triangular cross section, with intersection side walls coming together to define the respective vertices 23V2 and 24V2. The vertices are rounded and otherwise do not define a knife edge, in the implementation illustrated. The contact points lie in substantially the same sagittal plane but are offset slightly in the axial plane, with the contact points being on the inner portions of the respective condyles proximate the intercondylar fossa. Relative to JCP7 and JCP8, the separation between the condyles at JCP9 and JCP10 is greater. Contact points JCP9 and JCP10 can move posteriorly but are constrained from moving anteriorly when the jig is seated. Depending on the shape of the condyles where contact is made at JCP7-JCP10, it is possible that some of the jig contact points may not be constrained posteriorly or anteriorly, or not all of the points make contact.

Figure 10A:
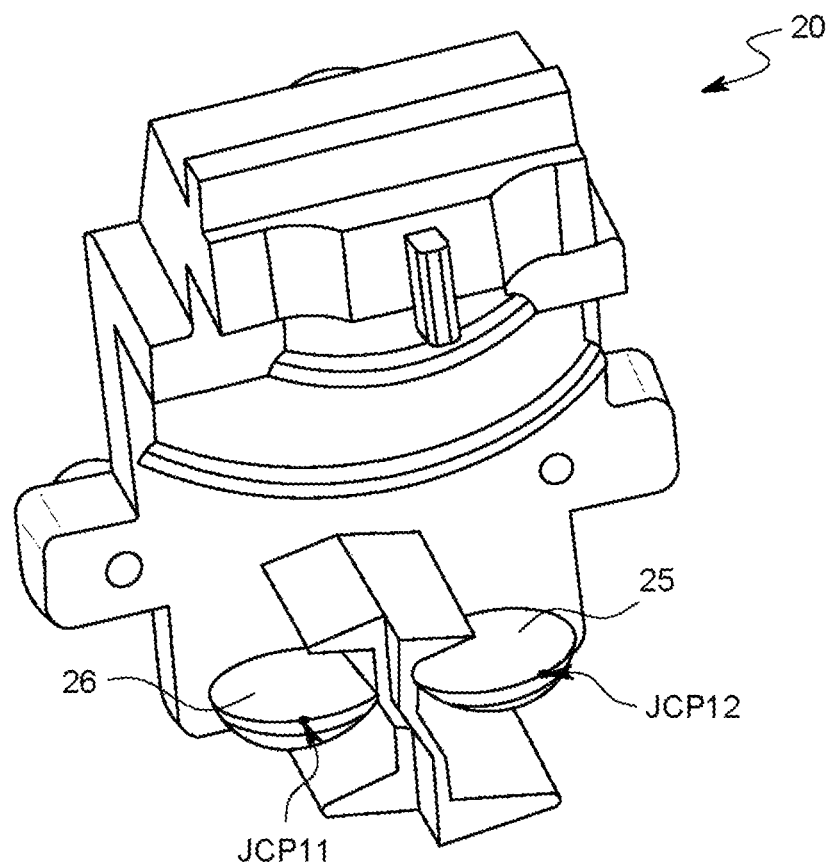
FIGS. 10A-10B are isometric and schematic views indicating suitable locations of FCJM contact points (11-12), according to an embodiment.
Figure 10B:
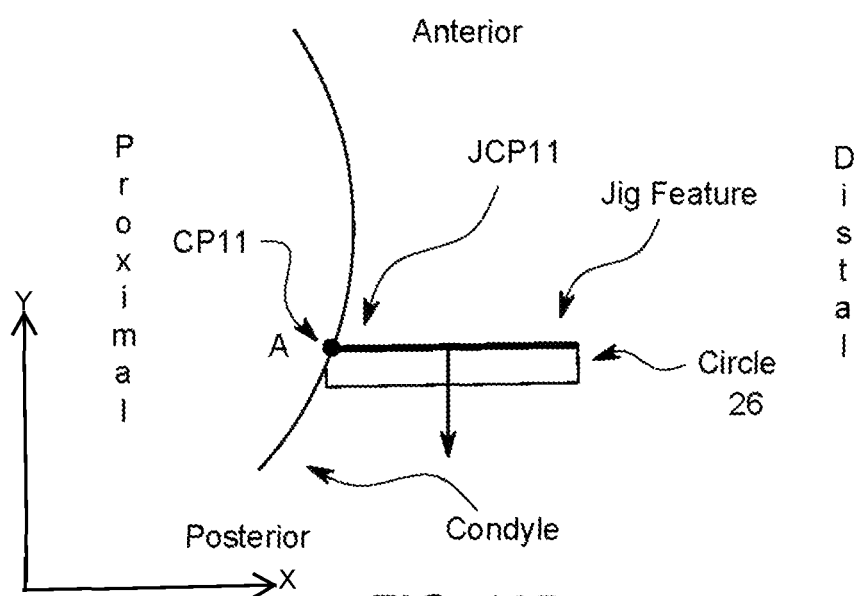

FIGS. 10A and 10B are isometric and schematic views of the jig 20, showing one or two suitable positions for jig contact points, JCP11 and JCP12. The jig contact points JCP11 and JCP12 lie on the first and second circle sectors, 25 and 26 (FIG. 2A). As indicated in a sagittal view of a portion of the trochlear groove 14, with the jig in contact with the femur lower portion (FIG. 10B), each of the jig contact points, JCP11 and JCP12, can move posteriorly (indicated by vertical arrow), but cannot move anteriorly, because of the presence of a solid object, a portion of one or the other condyle, LC and/or MC. JCP11 and JCP12 are in the same or substantially the same sagittal plane as JCP9 and JCP10 in the embodiment illustrated.

The contact points CP1, CP2, CP3, CP4, CP5 and/or CP6 are associated with features of the trochlear groove and condyle features adjacent thereto, and the contact points CP7, CP8, CP9, CP10, CP11 and/or CP12 are associated with features of one or both of the condyles adjacent to and posterior from the intercondylar fossa. One goal of the contact points on the jig 20 is to provide an optimal position of the jig in contact with the distal femur for which lateral rotation (posterior to anterior, or anterior to posterior) of the jig relative to the lower femur, or longitudinal (sagittal) translation of the jig relative to the lower femur, or axial twisting (rotation) clockwise or counterclockwise is strongly resisted by friction. Stated differently, when the jig is properly positioned on the femur such that the jig contact points are touching the respective femoral contact points, the jig is firmly held on the femur through the intercooperation of the jig contact points to the femoral contact points. While it is possible, that a small number of the jig contact points, e.g., one or two, may not actually touch the femur due to actual femoral inconsistencies relative to the images of the femur, the jig will nonetheless be held in position.

Figure 11:
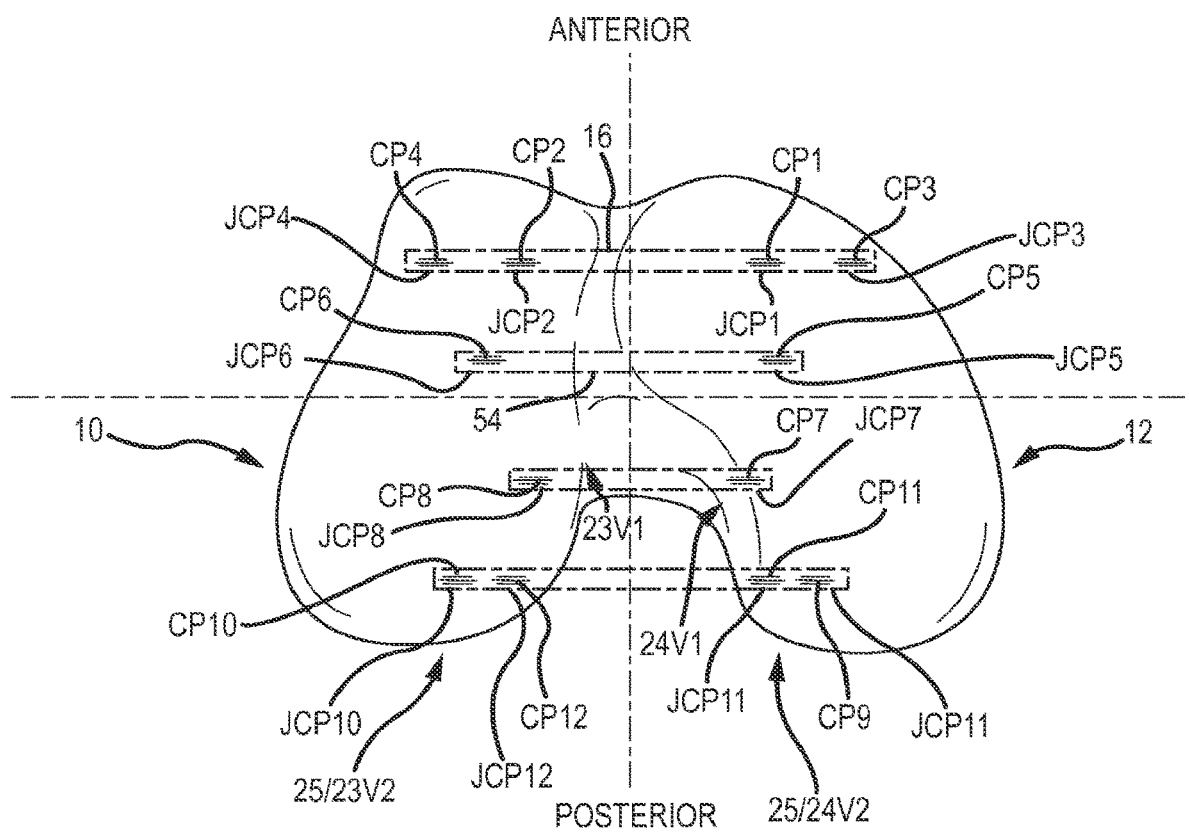
FIG. 11 is an axial view of a distal femur illustrating jig contact points and femoral contact points, according to an embodiment.

More specifically and as illustrated in FIG. 11, which is an axial representative view of the distal region of the femur and the jig contact surfaces and associated points, there are six contact points (JCP1-JCP6) constrained against posterior movement. The shape of the trochlear groove and condyles where JCP1-JCP6 contact the femur cooperatively constrain the jig from posterior movement. Similarly, there are six contact points (JCP7-JCP12) constrained against anterior movement. The shape of the condyles where JCP7-JCP12 contact the femur cooperatively constrain the jig from anterior movement. Further, CP1-CP6 cooperate with CP7-CP12 to constrain the jig from any form of anterior or posterior movement or rotation over the femur, by cooperatively opposing both posterior and anterior movement, respectively.

The jig is also held against rotational movement in the axial plane or twisting or canting off the sagittal plane. For perspective, if the femoral head above and adjacent the intercondylar fossa is considered along the axis of the femur, or relatively close, the contact points JCP1, JCP3 and JCP5 cooperate with JCP8, JCP10, and JCP12 to oppose rotational forces in the counterclockwise direction with the axis as reference. Similarly, the contact points JCP2, JCP4, and JCP6 cooperate with JCP7, JCP9 and JCP11 to oppose rotational forces in the clockwise direction with the axis as reference.

Referring primarily to FIG. 11, and discussing relative relationships between jig contact points anteriorly to posteriorly, it can be seen that the jig contact points JCP1, JCP2, JCP3 and JCP4 may be substantially coplanar in a coronal plane. Similarly, jig contact points JCP5 and JCP6 may be define a plane substantially parallel to the plane of JCP1-JCP3, JCP7 and JCP8 may define a plane substantially parallel with the place of JCP5 and JCP6, and JP9, JCP10, JCP11, and JCP12 may be substantially coplanar. As shown, the contact points defining planes or when defining planes are parallel, may lie in the same plane with possibly some deviation based on manufacturing tolerances or the like, and the defined planes may not be parallel also depending on manufacturing tolerances. The points, however, do not necessarily lie in a common transverse plane due to the contact point anatomies at the points. In some implementation, the contact points may be considered coplanar but be anterior or posterior (sagittally offset from illustrated) to a common plane by 2 millimeters. Of course, depending on patient anatomy, manufacturing efficiency, design considerations or the like, contact points may not be coplanar as described, and the planes may deviate from parallel based on optimal point positioning due to patient anatomy, joint degradation, MRI image quality and the like.

As illustrated, the contact points JCP1-JCP4, may be separated from JCP5, JCP6 by between about 15 millimeters (a range of 12-18 millimeters being typical). The contact points JCP5 and JCP6 are posteriorly relative to JCP1-JCP4. The contact points JCP5 and JCP6 may be separated from JCP7 and JCP8 by about 14 millimeters (a range of 11-17 millimeters being typical). The contact points JCP7 and JCP8 posterior relative to JCP5 and JCP6. The contact points JCP9-JCP12 may be separated from JCP7 and JCP8 be about 10 millimeters (a range of 7 to 13 millimeters being typical). The contact points JCP9-JCP12 are posterior relative to JCP7 and JCP8. The dimensions are from a sagittal plane to a sagittal plane, measured transversely (posteriorly) with reference to the orientation and arrangement illustrated in FIG. 11.

While the jig implementation illustrated includes 12 jig contact points, it is possible to provide a jig with slightly more or slightly less contact points. For example, JCP3 and JCP4 might be eliminated. In another example, JCP3 and JCP4 and/or JCP5 and JCP6 might be eliminated. In another example, JCP8 and JCP7 might be eliminated. In another example, JCP3 and JCP4, and/or JCP5 and JCP6, and JCP7 and JCP8 might be eliminated.

Additionally, it is possible to move the various points anteriorly or posteriorly relative to the positions indicated. Such movement may depend on damage to the knee being replaced, shape of the trochlear groove, shape of one or both condyles, the size of the femur, and the type of procedure being performed.

The embodiment shown contemplates a cut plane guide that is separately pinned to the femur so that the jig may be removed prior to resection. It is possible, however, to fabricate the cutting guide into the body of the jig and form a unified structure where the entirety of the jig is pinned to the femur and stays in place during the resectioning procedure. This embodiment contemplates the jig being of possibly different material (e.g., a sufficient hard polymer to receive a saw blade in the cut slot, or stainless steel). The jig may also include a cut guide, which may be integrated with the substrate or be provided by a cutting guide attached thereto that provides the cut guide, which may be in the form of a slot or other mechanism by which a surgeon may resect the femur along an established cut plane transverse the femoral axis and typically associated with a partial or total knee replacement procedure. It is also possible, depending on the material used for the jig, to place a liner within the cut slot of the cutting guide, where the liner is stainless steel such that the saw will not abrasively cut the slot during the back and forth sawing action. It is also possible for the slot to be integrated in the jig directly, in which case the cut plane guide will be a part of the jig.

The embodiment discussed above contemplates the use of pins to secure the jig and the cutting plane guide in place. It is possible, however, to use other forms of anchors such as screws or combinations of screws and pins. It is also possible, in the case of pins, to use some relatively small (smaller than threads of a screw) of some form of abrasive surface—e.g., annular ridges, roughing, or the like along some or all of the pin shaft, to ensure the pins stay in place and therefore holds the respective jig and/or cutting plane guide in place. Moreover, the jig is shown as defining a plurality of apertures, along with respective bosses, to receive such anchors. It is possible, however, to have the apertures defined in separate structures attached to or otherwise associated with the jig or to secure the jig to the femur in some other way, or to simply hold it in place while the cut plane guide is secured to the femur.

The following claims may reference various features of a jig or other structure in relation to various anatomical features of the tibia. Such anatomical features, however, are not intended to form part of the claim.

What is claimed is:

1. A cutting jig for positioning a femur cutting tool on a femur including a first condyle and a second condyle with a trochlear groove defined therebetween, the femur further including an intercondylar fossa, the cutting jig comprising:
 a substrate including:
 a first jig contact point oriented to contact the first condyle proximate the trochlear groove when the jig is positioned on the femur for a procedure;
 a second jig contact point oriented to contact the second condyle proximate the trochlear groove when the jig is positioned on the femur for a procedure, the second jig contact point coronally spaced apart from the first jig contact point;

a third jig contact point proximate the first jig contact point, the third jig contact point oriented to contact the first condyle when the jig is positioned on the femur for a procedure;

a fourth jig contact point proximate the second jig contact point when the jig is positioned on the femur for a procedure, the fourth jig contact point oriented to contact the second condyle;

a fifth jig contact point oriented to contact the first condyle when the jig is positioned on the femur for a procedure, the fifth jig contact point posteriorly positioned relative to the first jig contact point;

a sixth jig contact point oriented to contact the second condyle when the jig is positioned on the femur for a procedure, the fifth jig contact point posteriorly positioned relative to the second jig contact point; and a cut guide, wherein the first, second, third, fourth, fifth, and sixth jig contact points and their placements on the femur are chosen to allow the cutting jig to be positioned on the femur in a stable location and orientation such that the trochlear groove's shape and the first and second condyles where the first, second, third, fourth, fifth, and sixth jig contact points contact the femur cooperatively constrain the cutting jig from posterior movement, and wherein the first, second, third, fourth, fifth, and sixth jig contact points are determined using a plurality of two-dimensional MRI images or slices of an anatomical surface of the femur, with each MRI image or slice containing one or more spaced apart contact points between the anatomical surface of the femur and the cutting jig.

2. The cutting jig of claim 1 wherein at the least the first jig contact point is defined on a first curvilinear projection from the substrate.

3. The cutting jig of claim 2 wherein the first jig contact point and the second jig contact point are defined along the first curvilinear projection and wherein the first curvilinear projection defines a first semi-circle with a first radius.

4. The cutting jig of claim 3 wherein the third jig contact point and the fourth jig contact point are positioned along a first linear surface aligned with the first curvilinear projection.

5. The cutting jig of claim 3 wherein the fifth and sixth jig contact points are defined along a second curvilinear projection extending from the substrate, the second projection defining a second semi-circle with a second radius larger than the first radius.

6. The cutting jig of claim 5 wherein the first radius is about 15 millimeters and the second radius is about 18 millimeters.

7. The cutting jig of claim 1 further comprising a cutting guide support extending from the substrate, the cutting guide support positioned to retain the cutting guide.

8. The cutting jig of claim 7 wherein the cut guide is a slot configured to receive a saw to perform a resection of the femur, the slot positioned to orient the saw to cut transverse a femoral axis.

9. The cutting jig of claim 1 further comprising a first substrate portion and a second substrate portion, the first substrate portion substantially perpendicular the second substrate portion.

10. The cutting jig of claim 1 further comprising a plurality of apertures, wherein in each aperture is configured to receive a respective anchor to secure the jig to the femur.

* * * * *